(12) United States Patent
Daenen et al.

(10) Patent No.: US 9,561,170 B2
(45) Date of Patent: *Feb. 7, 2017

(54) HAIR CARE POLYMER

(71) Applicant: DSM IP ASSETS B.V., Heerlen (NL)

(72) Inventors: Robin Elisabeth Maria Jacobus Daenen, Basel (CH); Franciscus Johannes Marie Derks, Basel (CH); Dirk Weber, Basel (CH); Ruediger Wilz, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/424,680

(22) PCT Filed: Sep. 11, 2013

(86) PCT No.: PCT/EP2013/068807
§ 371 (c)(1),
(2) Date: Feb. 27, 2015

(87) PCT Pub. No.: WO2014/041019
PCT Pub. Date: Mar. 20, 2014

(65) Prior Publication Data
US 2015/0320670 A1   Nov. 12, 2015

(30) Foreign Application Priority Data

Sep. 17, 2012   (EP) .................... 12184650

(51) Int. Cl.
| | | |
|---|---|---|
| *C11D 1/62* | (2006.01) |
| *C08G 69/48* | (2006.01) |
| *A61Q 5/02* | (2006.01) |
| *A61K 8/88* | (2006.01) |
| *A61K 8/84* | (2006.01) |
| *A61Q 5/12* | (2006.01) |
| *A61K 8/73* | (2006.01) |
| *A61K 8/81* | (2006.01) |
| *C08G 73/02* | (2006.01) |

(52) U.S. Cl.
CPC ............... *A61K 8/84* (2013.01); *A61K 8/731* (2013.01); *A61K 8/817* (2013.01); *A61K 8/88* (2013.01); *A61Q 5/02* (2013.01); *A61Q 5/12* (2013.01); *C08G 73/02* (2013.01); *C08G 73/0293* (2013.01); *A61K 2800/5426* (2013.01); *A61K 2800/594* (2013.01)

(58) Field of Classification Search
CPC ....... C11D 1/62; C11D 3/3769; C08G 83/006; C08G 69/48; C08G 73/0293; A61Q 5/02; A61K 8/8164; A61K 8/88; A61K 2800/544; A61K 2800/5426
See application file for complete search history.

(56) References Cited

U.S. PATENT DOCUMENTS

2002/0165103 A1* 11/2002 Tsaur ...................... A61K 8/73
                                                          510/130
2010/0069601 A1*  3/2010 Baumer ................... A61K 8/88
                                                          528/322

FOREIGN PATENT DOCUMENTS

| CN | 102065833 | 5/2011 |
| WO | WO 2007/098888 | 9/2007 |
| WO | WO 2007/144189 | 12/2007 |
| WO | WO 2009/153333 | 12/2009 |
| WO | WO 2009/153334 | 12/2009 |

OTHER PUBLICATIONS

International Search Report for PCT/EP2013/068807 mailed Oct. 30, 2013, 3 pages.
R. Van Benthem et al., "Synthesis and Characterization of Bis(2-hydroxypropyl) amide-Based Hyperbranched Polyesteramides", Macromolecules, American Chemical Society, vol. 34, No. 11, May 22, 2001, 8 pages.

* cited by examiner

Primary Examiner — Brian P Mruk
(74) Attorney, Agent, or Firm — Nixon & Vanderhye P.C.

(57) ABSTRACT

The invention relates to a hair care composition comprising at least one cationic film forming polymer selected from the group of Polyquaternium and at least one quaternized hyperbranched polymer having end-groups of formula (I) characterized in that said quaternized hyperbranched polymer is obtainable by preparation of a hyperbranched polymer having dimethylamino end groups by condensation of 2-dodecen-1-ylsuccinic anhydride, diisopropanolamine and N,N-bis[3-(dimethylamino)propyl]amine followed by quaternization of the dimethylamino end-groups to end groups of formula (I).

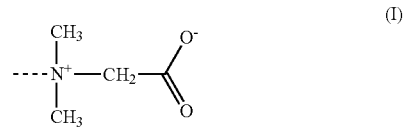

(I)

14 Claims, No Drawings

HAIR CARE POLYMER

This application is the U.S. national phase of International Application No. PCT/EP2013/068807, filed 11 Sep. 2013, which designated the U.S. and claims priority to EP 12184650.5, filed 17 Sep. 2012, the entire contents of each of which are hereby incorporated by reference.

The invention relates to a hair care composition comprising at least one cationic film forming polymer selected from the group of Polyquaternium and at least one quaternized hyperbranched polymer having end-groups of formula (I)

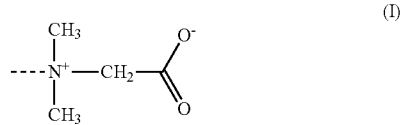

characterized in that said quaternized hyperbranched polymer is obtainable by preparation of a hyperbranched polymer having dimethylamino end groups by condensation of 2-dodecen-1-ylsuccinic anhydride, diisopropanolamine and N,N-bis[3-(dimethylamino)propyl]amine followed by quaternization of the dimethylamino end-groups to end groups of formula (I).

Many hair care compositions are known. However, so far it is very difficult to formulate hair care compositions which exhibit good wet care properties without changing or even improve the dry care properties. In particular there is a need for shampoo preparations which increase the volume of hair while exhibiting excellent dry and/or wet care properties i.e. dry and/or wet combing, wet feel and style setting. Furthermore, the shampoos should also result in improved dry properties i.e. improved visible volume and elasticity.

Surprisingly it has been found that shampoo preparations comprising specific quaternized hyperbranched polymers obtainable by condensation of 2-dodecen-1-ylsuccinic anhydride, diisopropanolamine and N,N-bis[3-(dimethylamino)propyl]-amine followed by quaternization of the dimethylamino end-groups of the resulting hyperbranched polymer with sodium 2-chloroacetate in combination with a cationic film forming polymer selected from the group of Polyquaternium fulfil the above mentioned requirements.

Thus, in one embodiment, the invention relates to hair care compositions comprising at least one cationic film forming polymer selected from the group of Polyquaternium and at least one quaternized hyperbranched polymer having end-groups of formula (I)

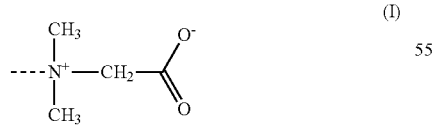

characterized in that said quaternized hyperbranched polymer is obtainable by
(i) preparation of a hyperbranched polymer having dimethylamino end groups by condensation of 2-dodecen-1-ylsuccinic anhydride, diisopropanolamine and N,N-bis[3-(dimethylamino)propyl]amine followed by
(ii) quaternization of the dimethylamino end-groups to end groups of formula (I).

Dotted lines indicate in the present document the binding site to other substituents.

In another embodiment the invention is directed to the use of hair care compositions according to the present invention for improving at the same time the volume, elasticity, wet feel, wet combing and style setting of hair.

Furthermore, the invention is directed to a method of treating hair, said method comprising the steps of applying a hair care composition according to the present invention to the hair followed by rinsing the hair with water. In particular the method is directed to the improvement of the volume, elasticity, wet feel, wet combing, and style setting of hair. In another preferred embodiment the method also includes the step of observing and/or appreciating the effect.

In a particular embodiment the hyperbranched polymers having dimethylamino end-groups are obtainable by condensation of 40-70 wt.-% of 2-dodecen-1-ylsuccinic anhydride, 5-20 wt.-% of diisopropanolamine and 15-45 wt.-% of N,N-bis[3-(dimethylamino)propyl]amine, in particular of 45-65 wt.-% of 2-dodecen-1-ylsuccinic anhydride, 8-18 wt.-% of diisopropanolamine and 20-40 wt.-% of N,N-bis[3-(dimethylamino)propyl]amine, most in particular of 55-65 wt.-% of 2-dodecen-1-ylsuccinic anhydride, 12-17 wt.-% of diisopropanolamine and 20-30 wt.-% of N,N-bis[3-(dimethylamino)propyl]amine with the proviso that the total amount of 2-dodecen-1-ylsuccinic anhydride, diisopropanolamine and N,N-bis[3-(dimethylamino)propyl]amine sums up to 100 wt.-%.

The terms 2-dodecen-1-ylsuccinic anhydride (CAS No. [19780-11-1]), diisopropanolamine (CAS No. [110-97-4]) and N,N-bis[3-(dimethylamino)propyl]-amine (CAS No. [6711-48-4]) as used herein refers to pure 2-dodecen-1-ylsuccinic anhydride, diisopropanolamine and N,N-bis[3-(dimethylamino)propyl]amine as well as to commercially available grades thereof. Such commercially available grades may contain a certain amount of impurities (commercially available technical grades) which preferably should not exceed 15 wt.-%, more preferably 10 wt.-% and most preferably 5 wt.-%.

2-Dodecen-1-ylsuccinic anhydride suitable for the purpose of the present invention is e.g. commercially available at Vertellus Chemiclas (Antwerpem, Belgium).

Suitable Diisopropanolamine for the purpose of the present invention is e.g. commercially available as Diisopropanolamine at BASF.

Suitable N,N-bis[3-(dimethylamino)propyl]amine for the purpose of the present invention is e.g. available at Huntsman Holland (Rotterdam, The Netherland as Tetramethyl iminobispropylamine).

In all embodiments of the present invention, it is preferred that the quaternized hyperbranched polymers having end groups of formula (I) are obtained by
(i) preparation of a hyperbranched polymer having dimethylamino end groups by condensation of 2-dodecen-1-ylsuccinic anhydride, diisopropanolamine and N,N-bis[3-(dimethylamino)propyl]amine followed by
(ii) quaternization of the dimethylamino end-groups to end groups of formula (I)
with all the preferences and definition given herein.

In all embodiments of the present invention it is furthermore preferred that the quaternization is carried out using sodium 2-chloroacetate (CAS No. [3926-62-3]).

The amount (mol %) of dimethylamino end-groups in the hyperbranched polymers depends on the ratio of the building blocks i.e. 2-dodecen-1-ylsuccinic anhydride, diisopropanolamine and N,N-bis[3-(dimethylamino)propyl]amine and can easily be calculated and adjusted by a person skilled in the art. Dependent on the ratio of the building blocks, the hyperbranched polymers having diemethylamino end-groups may further comprise —OH or —COOH end-groups. Preferably, the ratio of the building blocks is selected such that 50 to 100 mol % of all end-groups of the hyperbranched polymer having dimethylamino end-groups are dimethylamino end-groups and more preferably such that 70-100 mol % of all end-groups are dimethylamino end-groups.

The term "end-groups" as used according to the present invention generally refers to the groups at the periphery of the hyperbranched polymer. However, due to the complex structure of hyperbranched polymers such groups may also be sometimes located within the polymer.

In all embodiments of the present invention, the degree of quaternization of the dimethylamino end-groups is preferably selected in the range of 50 to 100 mol-%, more preferably in the range of 70 to 100 mol-%, most preferably in the range of 80 to 100 mol-% and in particular in the range of 85 to 100 mol-%.

It is well understood in the context of the present invention that instead of 2-dodecen-1-ylsuccinic anhydride, the respective di-acid i.e. 2-dodecen-1-yl succinic acid or a mixture of the anhydride and the di-acid can be used. The amounts and ratios given, however, would have to be adjusted accordingly. In all embodiments of the present invention, however, the use of 2-dodecen-1-ylsuccinic anhydride is preferred.

The quaternized hyperbranched polymers according to the present invention may be synthesized as e.g. outlined in WO 2007/098888 A1 or illustrated in the examples of the present invention.

The (theoretical) molecular weight of the hyperbranched polymers (before quaternization) can be adjusted via the ratio of the different building blocks used, in particular by the ratio of diisopropanolamine (branching unit) to 2-dodecen-1-ylsuccinic anhydride which can be easily selected by a person skilled in the art. The effect of N,N-bis[3-(dimethylamino)propyl]amine (chain stopper) on the molecular weight of the resulting polymer can also be calculated by a person skilled in the art.

The ratios are advantageously selected such that the hyperbranched polymers having dimethylamino end-groups exhibit a theoretical (i.e. calculated) average number molecular weight $M_n$ in the range of 1000 to 150,000 g/mol, more advantageously in the range of 1000 to 50,000 g/mol, most preferably in the range of 1500-5000 g/mol.

Therefore, in all embodiments of the present invention the ratio (w/w) of N,N-bis[3-(dimethylamino)propyl]amine to diisopropanolamine is preferably selected in the range of 4:1 to 0.5:1, more preferably in the range of 3:1 to 1:1. Most preferably N,N-bis[3-(dimethylamino)propyl]amine is used in a molar excess based on diisopropanolamine. Thus, most preferably, the ratio (w/w) of N,N-bis[3-(dimethylamino)propyl]amine to diisopropanolamine is selected in the range of 2.5:1 to 1.2:1, such as in the range of 2.2:1 to 1.2:1.

Also in all embodiments of the present invention, the ratio (w/w) of 2-dodecen-1-ylsuccinic anhydride to the total amount of amines (i.e. N,N-bis[3-(dimethylamino)propyl]amine and diisopropanolamine) is preferably selected in the range of 3:1 to 1:3, preferably in the range of 2:1 to 0.5:1. Most preferably in all embodiments of the present invention, 2-dodecen-1-ylsuccinic anhydride is used in an excess (w/w) based on the total amount of amines (i.e. the sum of N,N-bis[3-(dimethylamino)propyl]amine and diisopropanolamine) such as in a ratio (w/w) selected in the range of 2:1 to 1.2:1.

The condensation reaction of 2-dodecen-1-ylsuccinic anhydride, diisopropanolamine and N,N-bis[3-(dimethylamino)propyl]amine resulting in hyperbranched polymers having dimethylamino end-groups is advantageously carried out in an one-pot procedure. Preferably, the building blocks are charged stepwise into the reactor, such as e.g. exemplified in WO2007/098888 A1 example 1 to 3. The condensation reaction may be carried out at room temperature or at an elevated temperature. Preferably, the condensation reaction is carried out at a temperature selected in the range of about 100 to 250 C, more preferably in the range of 120 to 200° C. and most preferably in the range of 140 to 180° C. with water being removed, preferably through distillation. The one-pot procedure can take place with or without a solvent. Suitable solvents are organic solvents, such as methylisobutylketone, butylacetate, cyclohexane, methylcyclohexane, toluene or xylene. Preferably, no solvent is used. The removal of water can take place through distillation at reduced pressure, or, alternatively, may be removed azeotropically. Preferably, the water released during the condensation reaction is removed by vacuum (i.e. reduced pressure (<1013 mbar)). The condensation reaction advantageously takes place until >90% by weight, preferably >95% by weight or >98% by weight of the building blocks used are consumed.

The quaternization of the hyperbranched polymer having dimethylamino end groups is generally performed in water or any other suited solvent. Preferably the quaternization is performed in water. Thus, an advantageous process according to the present invention comprises dissolving the hyperbranched polymer having dimethylamino end-groups in water followed by addition of the quaternization reagent and heating the reaction mixture to a temperature selected in the range of 50-120° C. Preferably sodium 2-chloroacetate is used as quaternization reagent. The degree of quaternization depends on the amount of quaternization reagent used and can easily be calculated by a person skilled in the art dependent on the desired degree of quaternization. The ratio (w/w) of water to the hyperbranched polymer having dimethylamino end-groups is advantageously selected in the range 5:1 to 1:5, preferably in the range of 3:1 to 1:2, most preferably in the range of 2:1 to 1:1.

The polymer content of the aqueous solution resulting from the quaternization reaction is frequently 5 to 70 wt.-%, often 20 to 60 wt.-%, or 30 to 50 wt.-% and can be easily adjusted by a person skilled in the art by addition or removal of water.

The aqueous solution obtained from the quaternization reaction can either be incorporated directly into any aqueous, aqueous-alcoholic or alcoholic cosmetic preparation, such as for example a shampoo preparation, or drying of the solution takes place, e.g. spray-drying or freeze-drying, so that the hyperbranched polymer can be used and processed in the form of the neat polymer.

Preferably, the quaternized hyperbranched polymer according to the present is used as an aqueous solution having a polymer content selected in the range 5 to 70 wt.-%, more preferably in the range of 20 to 60 wt.-% and most preferably in the range of 30 to 50 wt.-%.

The amount of the at least one quaternized hyperbranched polymer in the hair care compositions according to the present invention is preferably selected in the range of 0.01-20 wt.-%, more preferably in the range of 0.05-10 wt.-% and most preferably in the range of 0.10 to 5 wt.-% such as in the range of 0.25 to 2 wt.-% based on the total weight of the hair care composition.

The term Polyquaternium (INCI Name) refers to polycationic polymers having quaternary ammonium centers in the polymer and which are used in the personal care industry. Particularly suitable Polyquaterniums for the purpose of the present invention are cationic cellulose derivatives including the polymeric quaternary ammonium salts of hydroxyethyl cellulose reacted with trimethyl or lauryl dimethyl ammonium-substituted epoxide, referred to in the industry (CTFA) as Polyquaternium-10 and Polyquaternium-24 and which are e.g. available from the Amerchol Corporation, for instance under the trade name Ucare™ Polymer JR or Ucare™ Polymer LM, or cationic diallyl quaternary ammonium-containing polymers including, for example, dimethyldiallylammonium chloride homopolymers as well as copolymers of acrylamide & dimethyldiallylammonium chloride, referred to in the industry (CTFA) as Polyquaternium-6 and Polyquaternium-7, respectively.

In all embodiments of the present invention the Polyquaternium is preferably selected from the group consisting of cationic cellulose derivatives and cationic diallyl quaternary ammonium-containing polymers as well as mixtures thereof, more preferably from the group consisting of polymeric quaternary ammonium salts of hydroxyethyl cellulose reacted with trimethyl or lauryl dimethyl ammonium-substituted epoxide, dimethyldiallylammonium chloride homopolymers and copolymers of acrylamide & dimethyldiallylammonium chloride as well as mixtures thereof, such as most preferably from the group consisting of Polyquaternium-7 and Polyquaternium-10 as well as mixtures thereof.

The amount of the at least one cationic film forming polymer selected from the group of Polyquaternium in the hair care compositions according to the present invention is preferably selected in the range of 0.01-5 wt.-%, more preferably in the range of 0.05-3 wt.-% and most preferably in the range of 0.2 to 1 wt.-% based on the total weight of the hair care composition.

In all embodiments of the present invention the hair care compositions are preferably shampoo preparations. The term shampoo preparation refers to hair cleansing preparations which are to be applied to the hair and then rinsed away.

The shampoo preparations according to the present invention preferably comprise from 50 to 98 wt.-%, more preferably from 60 to 90 wt.-% of water based on the total weight of the shampoo preparation. Furthermore, the shampoo preparations according to the present invention preferably further comprise an anionic surfactant.

Thus, in a particular embodiment, the present invention also relates to shampoo preparations comprising next to the at least one quaternized hyperbranched polymer and the at least one cationic film forming polymer selected from the group of Polyquaternium, water and an anionic surfactant. It is well understood that all the preferences and definitions for the quaternized hyperbranched polymer and the at least one cationic film forming polymer selected from the group of Polyquaternium given herein also apply to the shampoo preparations comprising these.

The ratio of the anionic surfactant to the quaternized hyperbranched polymer in the shampoo preparations of the present invention is preferably selected in the range of 20 to 1 to 1 to 1, in particular 10 to 1 to 5 to 1, such as in particular 8 to 1.

Exemplary anionic surfactants comprise alkylsulfate, alkylethersulfate, alkylsulfonate, alkylarylsulfonate, alkylsuccinate, alkylsulfosuccinate, N-alkoylsarkosinate, acyltaurate, acylisethionate, alkylphosphate, alkyletherphosphate, alkylethercarboxylate, alpha-olefinsulfonate, especially the alkali- and earth alkali salts, e.g. sodium, potassium, magnesium, calcium, as well as ammonium- and triethanol amine-salts. The alkylethersulfate, alkyletherphosphate and alkylethercarboxylate may comprise between 1 to 10 ethylenoxide or propylenoxide units, preferably 1 to 4 ethylenoxide-units per molecule. Suitable anionic surfactants are e.g. sodium laurylsulfate, ammonium lauryl sulfate, sodium lauryl ether sulfate (also known as sodium laureth sulfate), ammonium lauryl ether sulfate (also known as ammonium laureth sulfate), sodium lauroylsarcosinate, sodium oleyl succinate, ammonium lauryl sulfosuccinate, sodium dodecylbenzol sulfonate, triethanol amidodecylbenzol sulfonate or sodium laureth carboxylate. Particularly preferred anionic surfactants to be used in the shampoo preparations according to the present invention are sodium lauryl sulfate, ammonium lauryl sulfate, sodium lauryl ether sulfate and ammonium lauryl ether sulfate as well as mixtures thereof.

The total amount of anionic surfactant (as active ingredient) in the shampoo preparations according to the present invention is preferably selected in the range of 0.1 to 50 wt. %, more preferably in the range of 5-20 wt.-% based on the total weight of the shampoo preparation.

The shampoo preparations according to the invention can contain further ingredients to enhance the performance and/or consumer acceptability such as preservatives, antioxidants, fatty substances/oils, silicones, thickeners, softeners, emulsifiers, light-screening agents, antifoaming agents, moisturizers, fragrances, co-surfactants, fillers, sequestering agents, cationic-, nonionic- or amphoteric polymers or mixtures thereof, acidifying or basifying agents, dyes, colorants, pigments or nanopigments, pearlizers or opacifiers, organic or inorganic particles, viscosity modifiers, and natural hair nutrients such as botanicals, fruit extracts, sugar derivatives and/or amino acids or any other ingredients usually formulated into rinse off compositions. The necessary amounts of the adjuvants and additives can, based on the desired product, easily be chosen by a skilled artisan in this field and will be illustrated in the examples, without being limited hereto.

The shampoo preparations according to the present invention preferably include co-surfactants, to help impart aesthetic, physical or cleansing properties to the compositions.

Examples of co-surfactants are nonionic surfactants, which can be included in an amount ranging from 0.5 to 8 wt.-%, preferably from 2 to 5 wt.-% based on the total weight of the preparation. For example, representative nonionic surfactants that can be included into shampoo preparations according to the invention include condensation products of aliphatic ($C_8$-$C_{18}$) primary or secondary linear or branched chain alcohols with alkylene oxides, usually ethylene oxide and generally having from 6 to 30 ethylene oxide groups. Other representative nonionic surfactants include mono- or di-alkyl alkanolamides such as e.g. coco mono- or di-ethanolamide and coco mono-isopropanolamide. Further nonionic surfactants which can be included in shampoo preparations of the invention are the alkyl polyglycosides (APGs). Typically, the APG is one which comprises an alkyl group connected (optionally via a bridging group) to a block of one or more glycosyl groups such as e.g. Oramix NS 1O ex Seppic; Plantacare 818UP, Plantacare 1200 and Plantacare 2000 ex Cognisi.

Another example of co-surfactants are amphoteric or zwitterionic surfactants, which can be included in an amount (as active ingredient) ranging from 0.5 to about 8 wt.-%, preferably from 1 to 4 wt.-% based on the total weight of the shampoo preparation. Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoo preparations according to the present invention include lauryl amine oxide, cocodimethyl sulphopropyl betaine, lauryl betaine, cocamidopropyl betaine (CAPB), sodium cocoamphoacetate and disodium cocoamphodiacetate. Particularly preferred amphoteric or zwitterionic surfactant to be used in the shampoo preparations of the present invention are cocamidopropyl betaine and disodium cocoamphodiacetate as well as a mixture thereof.

Thus, in a further advantageous embodiment the invention relates to shampoo preparations comprising at least one quaternized hyperbranched polymer with all the definitions and preferences as given above, at least one cationic film forming polymer selected from the group of Polyquaternium with all the definitions and preferences as given above, further comprising water, an anionic surfactant and an amphoteric or zwitterionic surfactant.

In an even more advantageous embodiment, the anionic surfactant is selected from the group consisting of sodium lauryl sulfate, ammonium lauryl sulfate, sodium lauryl ether sulfate and ammonium lauryl ether sulfate as well as mixtures thereof and the amphoteric or zwitterionic surfactant is selected from cocamidopropyl betaine and disodium cocoamphodiacetate as well as a mixture thereof.

In a particular preferred embodiment, the shampoo preparations according to the present invention only contain anionic surfactants selected from the group consisting of sodium lauryl sulfate, ammonium lauryl sulfate, sodium lauryl ether sulfate and ammonium lauryl ether sulfate as well as mixtures thereof and amphoteric or zwitterionic surfactants selected from cocamidopropyl betaine and disodium cocoamphodiacetate as well as mixtures thereof as surfactants.

In all embodiments of the present invention, the total amount of surfactants (including any co-surfactants/based on active content) in the shampoo preparations according to invention is generally selected in the range of 1 to 50 wt.-%, preferably in the range of 2 to 40 wt.-%, more preferably in the range of 5 to 25 wt.-%, such as in particular in the range of 9 to 15 wt.-% based on the total weight of the shampoo preparation.

The compositions according to the invention may also comprise a hydrotrope. A hydrotrope is a substance that improves the solubility of surfactants in water. Examples of hydrotropes are sodium xylene sulfonate, ammonium xylene sulphonate, sodium p-toluene sulfonate, sodium chlorobenzene sulfonate, sodium salicylate, proline, pyrogallol, resorcinol and urea. If used, preferably sodium xylene sulfonate is used as hydrotrope. The total amount of the hydrotrope in the shampoo preparations according to the invention preferably ranges from 0.1 to 30 wt.-%, preferably from 0.5 to 20 wt.-%, in particular from 1 to 5 wt.-% based on the total weight of the shampoo preparation.

The shampoo preparations of the invention may further comprise a suspending agent. Suitable suspending agents are selected from cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polymers of acrylic acid cross-linked with a polyfunctional agent may also be used; they are available commercially as Carbopol 934, Carbopol 941, Carbopol 980 and Carbopol Ultrez 10 Polymer. Examples of suitable copolymers of a carboxylic acid containing monomer and acrylic acid esters are Carbopol 1342, Carbopol Ultrez 20 or Carbopol Ultrez 21, Pemulen TR1 or Pemulen TR2. All Carbopol or Pemulen (trademark) materials are available from Lubrizol Advanced Materials.

A suitable heteropolysaccharide gum is xanthan gum, for example Keltrol-types or Kelzan-types from Kelco, Vanzan NF from RT Vanderbilt Inc. or Rhodicare-types from Rhodia.

Mixtures of any of the above suspending agents may be used. Preferred is a mixture of cross-linked polymer of acrylic acid and crystalline long chain acyl derivative.

If present, the total amount of the suspending agent(s) is preferably selected in the range of 0.1 to 10 wt.-%, more preferably in the range of 0.5 to 6 wt.-%, most preferably in the range of 0.9 to 4 wt.-% based on the total weight of the composition.

The shampoo preparations of the invention may comprise further conditioning agents to further optimize wet and dry conditioning benefits.

Particularly preferred further conditioning agents are silicone emulsions. Suitable silicone emulsions include those formed from silicones such as polydiorganosiloxanes, in particular polydimethylsiloxanes which have the CTFA designation dimethicone, polydimethyl siloxanes having hydroxyl end-groups which have the CTFA designation dimethiconol, and amino-functional polydimethyl siloxanes which have the CTFA designation amodimethicone. Suitable silicone emulsions for use in compositions of the invention are available from suppliers of silicones such as Dow Corning, Momentive Performance Materials, KCC or Wacker.

If used, the total amount of silicone(s) (as active) is preferably selected in the range of will 0.05 to 10 wt.-%, more preferably in the range of 0.05 to 5 wt.-%, most preferably in the range of 0.5 to 2 wt.-% based on the total weight of the shampoo preparation.

The shampoo preparations according to the invention may further contain anti dandruff agents. Examples of anti-dandruff agents which may be used are cimbazole, octopirox and zinc pyrithione. Customary film formers include, for example, chitosan, microcrystalline chitosan, quaternized chitosan, polyvinylpyrrolidone, vinyl pyrrolidone/vinyl acetate copolymers, polymers of quaternary cellulose derivatives containing a high proportion of acrylic acid, collagen, hyaluronic acid and salts thereof and similar compounds.

The shampoo preparations according to the invention may further contain UV-filter substances. Examples of UV-filter substances suitable for the incorporation into the compositions according to the invention include benzophenones such as e.g. benzophenones-4 or benzophenones-3, acrylates such as 2-ethylhexyl 2-cyano-3,3-diphenylacrylate (octocrylene, PARSOL® 340), cinnamate derivatives such as ethylhexyl methoxycinnamate (PARSOL® MCX), benzalmalonate derivatives bond to siloxanes such as e.g. polysilicones-15 (PARSOL® SLX), salicylate derivatives such as isopropylbenzyl salicylate, benzyl salicylate, butyl salicylate, ethylhexyl salicylate (PARSOL® EHS, Neo Heliopan OS), isooctyl salicylate or homomenthyl salicylate (homosalate, PARSOL® HMS, Neo Heliopan HMS), benzotriazole derivatives such as sodium benzotriazolyl butylphenol sulfonate, imidazole derivatives such as e.g. 2-phenyl benzimidazole sulfonic acid and its salts (PARSOL® HS), dibenzoylmethane derivatives such as (avobenzone, Parsol® 1789) without being limited thereto.

The invention is further illustrated with reference to the following, non-limiting examples, in which all percentages are by weight based on total weight unless otherwise specified.

EXAMPLE 1A

Preparation of a Hyperbranched Polymer According to the Invention (PoE-1a)

232 g of N,N-bis[3-(dimethylamino)propyl]amine and 109.9 g molten diisopropanolamine were added to a glass reactor equipped with stirrer and condenser, and which can be heated by oil. To this mixture 458.1 g of molten 2-dodecen-1-ylsuccinic anhydride was added. After addition the mixture was slowly heated to 160° C. and 1 h later vacuum was applied to remove the reaction water. After 5 h the mixture was cooled obtaining a hyperbranched polymer having dimethylamine end-groups and a $M_n$ of 2200.

50 g of the hyperbranched polymer having dimethylamine end groups were subsequently dissolved in 66.3 g water and to this mixture 16.3 g sodium 2-chloroacetate (SMCA) was added. This mixture was reacted at 80° C. for approximately 10 hours while stirring after which the quaternized polymer solution was ready for use (polymer content 50 wt.-%). Calculated level of quaternized dimethylamino end-groups: 90%.

EXAMPLE 1B

Preparation of a Hyperbranched Polymer According to the Invention (PoE-1 b)

235 g of N,N-bis[3-(dimethylamino)propyl]amine and 160 g molten diisopropanolamine were added to a glass reactor equipped with stirrer and condenser, and which can be heated by oil. To this mixture 639 g of molten 2 dodecen-1-ylsuccinic anhydride was added. After addition the mixture was slowly heated to 160° C. and 1 h later vacuum was applied to remove the reaction water. After 5 h the mixture was cooled obtaining a hyperbranched polymer having dimethylamine end-groups and a Mn of 17400.

80 g of the hyperbranched polymer having dimethylamine end groups were subsequently dissolved in 99.6 g water and to this mixture 19.6 g sodium 2 chloroacetate (SMCA) was added. This mixture was reacted at 80° C. for approximately 10 hours while stirring after which the quaternized polymer solution was ready for use (polymer content 50 wt.-%). Calculated level of quaternized dimethylamino end-groups: 90%.

EXAMPLE 1C

Preparation of a Reference Hyperbranched Polymer (Methyl Quaternized) (PoE-1c)

235 g of N,N-bis[3-(dimethylamino)propyl]amine and 160 g molten diisopropanolamine were added to a glass reactor equipped with stirrer and condenser, and which can be heated by oil. To this mixture 639 g of molten 2 dodecen-1-ylsuccinic anhydride was added. After addition the mixture was slowly heated to 160° C. and 1 h later vacuum was applied to remove the reaction water. After 5 h the mixture was cooled obtaining a hyperbranched polymer having dimethylamine end-groups and a Mn of 17400.

25 g of the hyperbranched polymer having dimethylamine end groups were subsequently dissolved in 50 g water and to this mixture 7.3 g dimethylsulfate was slowly added. After 24 h the the quaternized polymer solution was ready for use (polymer content 33 wt.-%). Calculated level of quaternized dimethylamino end-groups: 95%.

EXAMPLE 2

Wet Combing Properties

A standard shampoo as outlined in table 1 was prepared by dissolving the polymers in water, addition of the surfactants, followed by addition of the preservative. The pH was adjusted with Citric Acid on pH=5.0-5.1 and the viscosity controlled by addition of sodium chloride water solution

TABLE 1

| Standard Shampoo | |
| --- | --- |
| Ingredient (INCI) | Wt.-%* |
| Polymer of Example 1a (PoE-1a) | See table 2 |
| Polyquaternium-7 (Polyquat-7) | See table 2 |
| Hydroxypropyl guar (HPG) (Reference) | See table 2 |
| Sodium Laureth Sulfate 28%/Water 72% | 35.0% |
| Cocamidopropyl Betaine 40%/Water 60% | 5.0% |
| Sodium Benzoate | 0.5% |
| Citric acid | 0.15% |
| Sodium Chloride | 1.5% |
| Water | q.a. |

*all given concentrations are based on the active ingredient

The wet combing properties were done according to SGS Fresenius standardized study setup: 5 hair swatches per shampoo sample (European Hair, weight: 2±0.3 g, length: 21 cm, color 4/0 medium brown, Kerling International Art.-Nr. 826530) were used for the determination of combing forces. All swatches were defined damaged by professional hair bleach. The hair swatches were pre-conditioned in water and washed with a 14% Sodium Laureth Sulfate (SLES) solution. The wet combing force was measured immediately after washing. The combing force of the hair was measured using a tensile testing machine (Zwick Z 1.0/TN1SSO) resulting in the value for the untreated swatches.

Then the swatches were then treated twice with a test item (shampoo; 0.5 ml/g hair), foamed for 1 min and left to rest for additional 2 min. After each foaming phase the test product was rinsed off for 1 min with water. Again, the wet combing force was measured immediately after washing.

The average work is calculated from the surface below the force-path plot in the measuring interval between 20 and 120 mm. The relative combing force (RCF) is calculated from the value of the untreated swatch $W_0$, and the value of the treated swatch $W_1$ according following expression: $RCF[\%]=(W_0-W_1)/W_0$. Negative values show a reduction in combing force, positive an increase.

TABLE 2

Results of the wet combing test

| PoE-1a | Polyquat-7 | HPG | RCF measured | RCF expected | Δ* |
|---|---|---|---|---|---|
| 0.5 wt.-% | — | — | −7.0% | — | — |
| 1.0 wt.-% | — | — | −7.0% | — | — |
| — | 0.2 wt. % | — | −6.0% | — | — |
| 0.5 wt.-% | 0.2 wt.-% | — | −28.0% | −13% | +15% |
| 1.0 wt.-% | 0.2 wt.-% | — | −20.0% | −13% | +7% |
| — | — | 0.25 wt.-% | −24% | — | — |
| 0.5 wt.-% | — | 0.25 wt.-% | −26% | −31% | −5% |
| 1.0 wt.-% | — | 0.25 wt.-% | −26% | −31% | −5% |

*Δ = −[(RCF measured) − (RCF expected)]

As can be retrieved from the results outlined above only the inventive combination leads to a synergistic improvement of the wet combing properties, whereas the combination with another film forming polymer (i.e. Hydroxypropyl guar (HPG)) even results in a declined wet combability compared to the untreated swatches.

EXAMPLE 2

Stylist Salon Test

The Stylist Salon Test was done at AR Hair Cosmetics (Impasse du Nouveau-Marché, CH-1723 Marly). All products were tested with half-head comparison test vs. a reference comprising only the respective Polyquaternium. Test pairs were blinded, order and head side were randomized.

Tested Products

The effect of the combination of the polymer of example 1 with Polyquaternium-10 respectively Polyquaternium-7 was tested in the standard shampoo formulation as outlined in table 3.

TABLE 3

Shampoo formulations for half side test

| Ingredient (INCI) | A | A' (Ref) | B | B' (Ref) |
|---|---|---|---|---|
| | Wt.-%* | | | |
| Polymer of Example 1 | 0.5 | — | 1.0 | — |
| Polyquaternium-7 | 0.2 | 0.2 | — | — |
| Polyquaternium-10 | — | — | 0.4 | 0.4 |
| Sodium Laureth Sulfate 28%/Water 72% | 35.0 | 35.0 | 35.0 | 35.0 |
| Cocamidopropyl Betaine 40%/Water 60% | 5.0 | 5.0 | 5.0 | 5.0 |
| Sodium Benzoate | 0.5 | 0.5 | 0.5 | 0.5 |
| Citric acid | 0.15 | 0.15 | 0.15 | 0.15 |
| Sodium Chloride | 1.5 | 1.5 | 1.5 | 1.5 |
| Water | q.a. | q.a. | q.a. | q.a. |

*all given concentrations are based on the active ingredient

Definition of Difference in Evaluation

The values given in table 4 are the result of a direct comparison test of A with A' and B with B', wherein the references A' and B' have been set to 0 according to standard practice.

similar, 0 no difference slight, +/−1 Difference is not detectable without direct comparison. So this is without relevance in daily practice. Consequences are not expected.

noticeable, +/−2 Difference is so big, that it could also be detected without direct comparison.

TABLE 4

Results of the half side test

| | | | Attribute | | |
|---|---|---|---|---|---|
| Sample | Volume | Elasticity | Wet feel | Wet combing | Style setting |
| A | 1.5 | 1.4 | 1.0 | 0.9 | 1.1 |
| B | 1.5 | 2.0 | 1.6 | 1.8 | 1.0 |

The use of the shampoos comprising the combination of the specific polymers according to the present invention led in both cases to better care properties. Furthermore, the setting of a style with these shampoos was easier because the hair takes the desired shape good and stays better. Furthermore, these shampoos gave to water wave-hair-dos better bounce (elasticity) and more defined curls.

EXAMPLE 4

Comparative Test

A standard shampoo as outlined in table 5 was prepared by dissolving the polymers in water, addition of the surfactants, followed by addition of the preservative. The sodium chloride is dissolved in 4 parts water before adding. The pH was adjusted with Citric Acid on pH=4.8-5.1.

TABLE 5

Standard Shampoos

| Ingredient (INCI) | Wt.-%* | Wt.-%* |
|---|---|---|
| Polymer of Example 1b (PoE-1b) (Invention) | 1.0% | — |
| Polymer of Example 1c (PoE-1c) (Reference) | — | 1.0% |
| Sodium Laureth Sulfate 28%/Water 72% | 35.0% | 35.0% |
| Cocamidopropyl Betaine 40%/Water 60% | 5.0% | 5.0% |
| Sodium Benzoate | 0.5% | 0.5% |
| Citric acid | 0.5% | 0.5% |
| Sodium Chloride | 1.5% | 1.5% |
| Water demin. | Ad 100 | Ad 100 |

*all given concentrations are based on the active ingredient

Preparation of Swatches

The tresses (Caucasian, dark blond, virgin hair, 23 cm long, Kerling International Art. No. 826500) are cut in swatches of 2.0 cm width. Before washing, the hair swatches are soaked in 2-Propanol for ½ hour. Afterwards, the swatches were washed with a cleansing shampoo (35 wt.-% Sodium Laureth Sulfate 28%/Water 72%; 4% sodium chloride; 59.8 wt.-% water demin; 0.5 wt.-% sodium benzoate) as outlined below under application of product.

After washing, the hairs were combed, air dried and conditioned overnight in the climate chamber at 20° C. and 60% rel. humidity. The weight of the hair switches is standardized under these conditions for 2.4 g+/−0.2 g (representing ≈2.2 g of hair without rubber coating).

The hair swatches are measured (see below) without product application and assorted to groups with similar average combing force Application of Product Each swatch (ca. 2 g of hair) is wetted with warm tap water. 0.5 ml of shampoo according to table 5 (0.25 mL/g hair) is applied with a syringe from the root to the tips, and the shampoo is foamed with the fingers for a period of 30 sec. Then the swatch is rinsed under warm running tap water (38° C., ca. 5 l/min) for 30 sec, during rinsing, the shampoo is stripped-off carefully with the fingers. The procedure is done twice.

Measurement of Dry Combing Properties

The hairs are combed in wet stage and dried hanging without blow-drying for 3 hours in the lab. After that the hairs are stored in a climate chamber at 20° C. and 60% rel. humidity for at least 8 hours. Afterwards the dry combing force is measured using a INSTRON 5542, equipped with a pneumatic clamp. For the combing force measurement a combing rack is attached at the machine. The hair swatch is fixed in the clamp and pulled 10 times through the comb fixed at the rack with a velocity 500 cm/min.

The average work is calculated from the surface below the force-path plot in the measuring interval between 20 and 120 mm. The relative combing force (RCF) is calculated from the value of the untreated swatch $W_c$, and the value of the treated swatch $W_1$ according following expression: $RCF[\%] = (W_0 - W_1)/W_0$. Negative values show a reduction in combing force, positive an increase.

TABLE 6

| PoE-1b | Polyquat-7 | PoE-1c | RCF measured |
|---|---|---|---|
| 1.0 wt.-% | — | — | −10% |
| 1.0 wt.-% | 0.4 wt. % | — | −27% |
| — | — | 1.0 wt.-% | −10% |
| — | 0.4 wt.-% | 1.0 wt.-% | −8% |

As can be retrieved from the results outlined above only the inventive combination leads to a synergistic improvement of the dry combing properties, whereas the combination with the corresponding methyl quaternized hyperbranched polymer (i.e. PoE-1c) even results in a declined dry combability compared to the untreated swatches.

The invention claimed is:

1. A hair care composition comprising:
   (1) at least one polyquaternium as a cationic film forming polymer, and
   (2) at least one quaternized hyperbranched polymer having end-groups of formula (I):

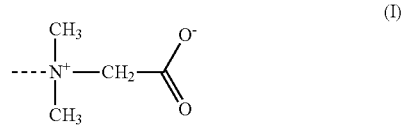

(I)

wherein the quaternized hyperbranched polymer is:
   (i) a condensation reaction product of a monomeric mixture consisting of 2-dodecen-1-ylsuccinic anhydride, diisopropanolamine and N,N bis[3-(dimethylamino)propyl]amine to obtain a hyperbranched polymer having dimethylamino end groups followed by
   (ii) quaternization of the dimethylamino end-groups to end groups of formula (I).

2. The hair composition according to claim 1, wherein the hyperbranched polymer having dimethylamino end-groups is a condensation reaction product of 40-70 wt.-% of 2 dodecen-1-ylsuccinic anhydride, 5-20 wt.-% of diisopropanolamine and 15-45 wt.-% of N,N-bis[3-(dimethylamino)propyl]amine with the proviso that the total amount of 2 dodecen-1-ylsuccinic anhydride, diisopropanolamine and N,N-bis[3-(dimethylamino)propyl]amine sums up to 100 wt.-%.

3. The hair composition according to claim 1, wherein the quaternization of the dimethylamino end-groups is carried out using sodium 2 chloroacetate.

4. The hair composition according to claim 1, wherein the degree of quaternization of the dimethylamino end-groups is in a range of 50 to 100 mol-%.

5. The hair composition according to claim 1, wherein a ratio (w/w) of N,N-bis[3-(dimethylamino)propyl]amine to diisopropanolamine is in a range of 4:1 to 0.5:1.

6. The hair composition according to claim 5, wherein the ratio (w/w) of N,N-bis[3-(dimethylamino)propyl]amine to diisopropanolamine is in the range of 2:5 to 1.2:1.

7. The hair composition according to claim 1, wherein a ratio (w/w) of 2-dodecen-1-ylsuccinic anhydride to the total amount of amines is in a range of 3:1 to 1:3.

8. The hair composition according to claim 1, wherein the hyperbranched polymer having dimethylamino end-groups has an average number molecular weight Mn which is in a range of 1500-5000 g/mol.

9. The hair composition according to claim 1, wherein at least one quaternized hyperbranched polymer is present in an amount within a range of 0.01-20 wt.-%.

10. The hair composition according to claim 1, wherein the at least one cationic film forming polymer is selected from the group consisting of cationic cellulose derivatives, cationic diallyl quaternary ammonium-containing polymers and mixtures thereof.

11. The hair composition according to claim 1, wherein the at least one cationic film forming polymer is present in an amount within a range of 0.01-5 wt. %.

12. The hair care composition according to claim 1, wherein the hair care composition is a shampoo preparation.

13. A method of treating hair, said method comprising the steps of applying a hair care composition according to claim 1 to the hair followed by rinsing the hair with water.

14. The method according to claim 13, wherein the treatment of hair is an improvement of the volume, elasticity, wet feel, wet combing, and style setting of hair.

* * * * *